USO05611353A

United States Patent [19]
Dance et al.

[11] Patent Number: 5,611,353
[45] Date of Patent: Mar. 18, 1997

[54] METHOD AND APPARATUS FOR LOCATING FUNCTIONAL STRUCTURES OF THE LOWER LEG DURING KNEE SURGERY

[75] Inventors: Mark N. Dance; Aldo T. Salvestrao; Geoffrey F. Auchinleck, all of Vancouver, Canada

[73] Assignee: Osteonics Corp., Allendale, N.J.

[21] Appl. No.: 585,601

[22] Filed: Jan. 16, 1996

Related U.S. Application Data

[63] Continuation of Ser. No. 449,574, May 24, 1995, abandoned, which is a continuation of Ser. No. 81,028, Jun. 21, 1993, abandoned.

[51] Int. Cl.⁶ ............................................. A61B 5/103
[52] U.S. Cl. .................................. 128/782; 606/102
[58] Field of Search ............................ 128/774, 779, 128/782; 606/102

[56] References Cited

U.S. PATENT DOCUMENTS

| | | | |
|---|---|---|---|
| 4,467,801 | 8/1984 | Whiteside | 128/303 R |
| 4,474,177 | 10/1984 | Whiteside | 128/303 R |
| 4,524,766 | 6/1985 | Petersen . | |
| 4,558,697 | 12/1985 | Wu | 128/303 R |
| 4,571,834 | 2/1986 | Fraser et al. | 33/1 PT |
| 4,574,794 | 3/1986 | Cooke | 128/92 H |
| 4,739,751 | 4/1988 | Sapega | 128/92 V |
| 4,773,407 | 9/1988 | Petersen | 128/92 VW |
| 4,935,023 | 6/1990 | Whiteside et al. | 606/88 |
| 4,938,762 | 7/1990 | Wehrli | 606/88 |
| 4,950,271 | 8/1990 | Lewis | 606/102 |
| 4,969,895 | 11/1990 | McLeod | 606/96 |
| 4,979,949 | 12/1990 | Matsen, III et al. | 606/53 |
| 5,002,545 | 3/1991 | Whiteside et al. | 606/80 |
| 5,007,912 | 4/1991 | Albrektsson et al. | 606/87 |
| 5,071,420 | 12/1991 | Paulos | 606/99 |
| 5,122,145 | 6/1992 | Fishbane | 606/102 |
| 5,141,512 | 8/1992 | Farmer | 606/87 |
| 5,154,717 | 10/1992 | Matsen, III et al. | 606/53 |
| 5,289,826 | 3/1994 | Kovacevic | 128/774 |
| 5,318,571 | 6/1994 | Benson | 606/102 |
| 5,364,401 | 11/1994 | Ferrante | 606/84 |
| 5,385,567 | 1/1995 | Goble | 606/96 |
| 5,409,489 | 4/1995 | Sioufi | 606/80 |
| 5,411,503 | 5/1995 | Hollstien | 606/86 |
| 5,520,694 | 5/1996 | Dance et al. | 606/86 |

FOREIGN PATENT DOCUMENTS

| | | |
|---|---|---|
| 0322363 | 6/1989 | European Pat. Off. . |
| 0326768A2 | 8/1989 | European Pat. Off. . |
| 0466659 | 1/1992 | European Pat. Off. . |
| 2587198 | 3/1987 | France . |
| WO-8807840 | 10/1988 | WIPO . |

*Primary Examiner*—Max Hindenburg
*Attorney, Agent, or Firm*—Lerner, David, Littenberg, Krumholz & Mentlik

[57] ABSTRACT

Method and apparatus for locating functional structures of the lower leg during knee implant surgery by determining the location of the weight-bearing axis. The functional center of the hip is located by fixing the acetabulum of the patient, rotating the femur about its head to several locations, measuring changes of position of a reference point on the femur and computing an imaginary sphere having a center corresponding to the location of the functional center of the hip.

11 Claims, 7 Drawing Sheets

FIG. 1A
FIG. 1B
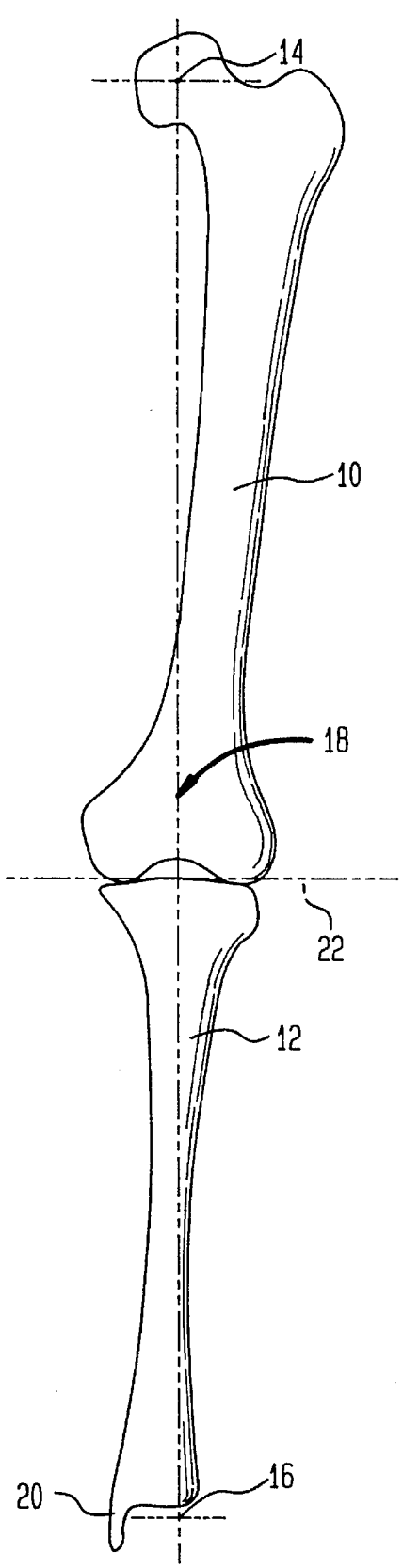
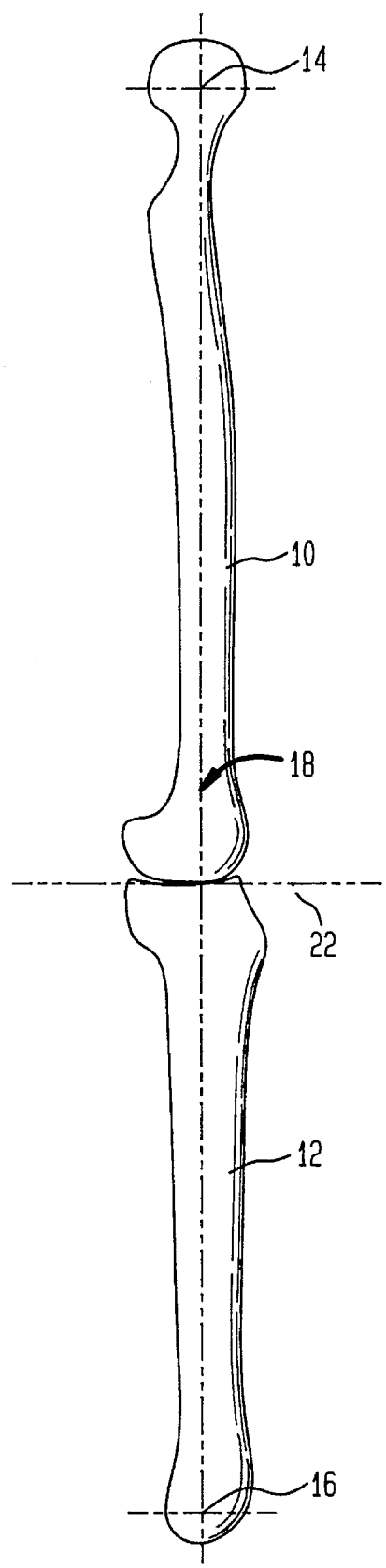

METHOD AND APPARATUS FOR LOCATING FUNCTIONAL STRUCTURES OF THE LOWER LEG DURING KNEE SURGERY

This application is a file wrapper continuation application of application Ser. No. 08/449,574 filed May 24, 1995, now abandoned, which application was a file wrapper continuation application of application Ser. No. 08/081,028, filed on Jun. 21, 1993, now abandoned.

FIELD OF THE INVENTION

The current invention relates to surgical methods and devices and specifically relates to an improved technique and apparatus for locating the alignment points of the leg during knee implant surgery.

BACKGROUND TO THE INVENTION

During knee implant surgery, more specifically known as knee arthroplasty, damaged or diseased bone is replaced with metal or plastic components to restore the function of the effected joint. Improvements in materials used in these implants have resulted in widespread acceptance of this surgical procedure.

A primary goal of knee arthroplasty is the proper placement of the components with respect to the anatomy of the patient. This placement is necessary so that proper implant function is achieved and the life of the implant optimized. In a human, the weight of the body passes along 8 theoretical line, sometimes referred to as the weight bearing axis or WBA, from the center of the hip joint to the center of the ankle joint. In a correctly functioning knee, the WBA passes through the center of the knee in both anterior/posterior planes and medial/lateral planes. In a knee exhibiting varus deformity the WBA passes medial to the center of the knee while in a knee exhibiting valgus deformity it passes lateral to the center of the knee. Location of the WBA during the knee arthroplasty therefore relies on the location of the center of the hip joint (the center of the head of the femur), the center of the knee, and the center of the ankle.

In addition to locating the WBA, the position of the implants along the WBA and their rotation around the WBA must be established. A horizontal line passing through the articular surface of the knee, referred to as the joint line, can be used to position the implants along the WBA. To rotationally locate the implants in the horizontal plane, several different anatomic landmarks are commonly used such as the location of he posterior or anterior femoral condyles or the location of the femoral epicondyles.

Most current techniques for locating the WBA can be grouped into one o two categories extramedullary or EM alignment; and, intramedullary of IM alignment.

EM alignment requires that the surgeon visually align slender, parallel rods from the knee joint to the head of the femur and the center of the ankle. The position of the head of the femur may be approximated either by palpation or with intraoperative X-ray. Location of the ankle rod can be approximated either with a notched device intended to seat around the ankle or with visual placement of the rod with respect to the palpated malleoli of the ankle. Once correctly positioned, the hip and ankle rods should lie parallel to the patient's WBA.

IM alignment replaces visually located rods with rods placed in the medullary canals of the femur and tibia. If properly placed, these rods should lie on the axis of the bones. Due to the offset of the femur at the hip, the bone axis is not the same as the WBA, therefore a correction must be made at operation to adjust the IM axis to estimate the WBA. This correction requires a preoperative X-ray be taken showing the angular difference between the femoral axis and the WBA.

EM alignment provides only visual estimation of the location of the WBA. It is subject to many errors and requires considerable surgeon-skill. Intraoperative location of the head of the femur is especially error prone. Palpation of the femoral head, complicated by patient obesity and sterile drapes placed over the patient, has been shown to be commonly inaccurate by 2–3 inches in comparison to radiographic location. Templates have been devised to assist radiographic location but the use of radiographs in the OR suite is time-consuming, awkward and exposes personnel to radiation. Additionally, any form of radiographic location is subject to distortion and requires a visual estimate of the location of anatomic landmarks which are not necessarily he kinematic centers of movement or of force transmittal.

IM alignment requires some skill in placing the rods. The placement of rods into the femur and tibia has been related to patient death from fat or gas embolism. The adjustment angle required o correct the IM axis to the WBA is commonly measured from a preoperative X-ray and, as result, is subject to distortion, reading errors and visual estimation problems as previously described.

What is required then, is a method for accurately and imply locating the true location of a patient's WBA determined by the kinematic position of the patient's joints. The method should be applicable to intraoperative applications. Preferably the method developed would not involve additional modification of the bone, other than that necessary for performing the procedure, could provide for preoperative planning and postoperative evaluation, and could be used to predict the effect of changes to the surgical protocol upon the results of the surgery.

SUMMARY OF THE INVENTION

Provided by the current invention are method and apparatus for determining the location of the WBA, for determining the preferred location of a knee implant, and for guiding the instruments used in the shaping of bone required to locate the implant.

Also provided are method and apparatus for locating the kinematic center of rotation of the hip joint involving the measurement in three dimensions of at least four discrete positions of the femur.

Further provided by the current invention are method and apparatus for measuring the position of the center of the ankle with respect to the femur and for estimating the instantaneous center of rotation for the knee with respect the ankle.

The method and apparatus provide are applicable to intraoperative application, do not involve additional modification of the patient's bone or tissue, other than that necessary for performing the procedure, provide for preoperative planning and postoperative evaluation, and can be used to predict the effect of changes to the surgical protocol upon the results of the surgery.

BRIEF DESCRIPTION OF THE DRAWINGS

FIGS. 1a and 1b shows the anatomic relationship of the weight bearing axis to a human femur and tibia.

DESCRIPTION OF THE EMBODIMENT

Figure 2A:
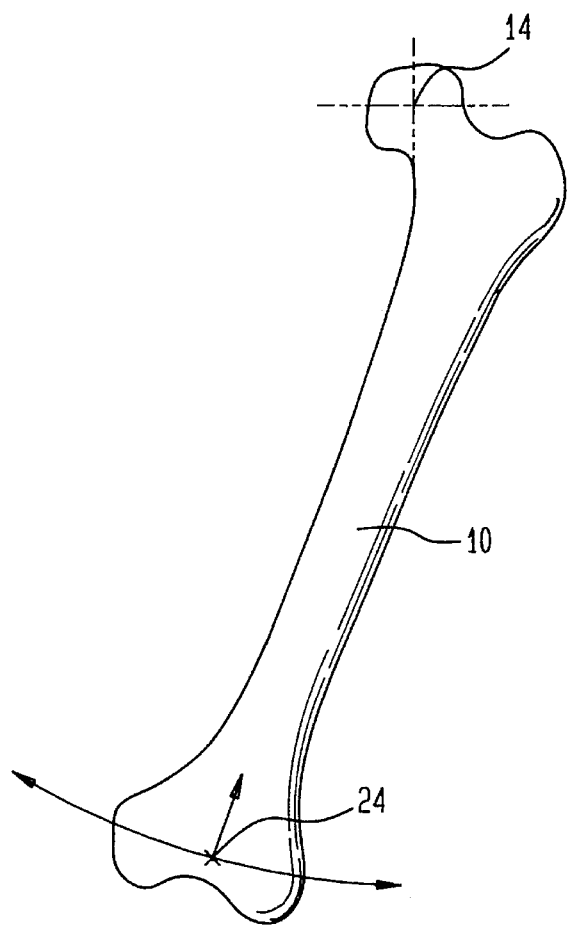
FIGS. 2a and 2b show the kinematic motion of the femur around the hip joint.

FIGS. 1a and 1b show in schematic form the relationship of the weight bearing axis (WBA) 18 to a left human femur 10 and tibia 12 in normal stance. FIG. 1a is a schematic in the coronal (medial-lateral) plane of the patient and FIG. 1b is in the sagital (anterior-posterior) plane of the patient.

Weight bearing axis 18 is defined to pass through two points: the center of the hip joint 14 and the center of the ankle joint 16. Weight bearing axis 18 normally passes slightly medial to the anatomic center of the knee joint although this may very considerably from patient to patient.

Hip joint center 14 is defined as the center of rotation of the hip joint and is generally accepted to be the anatomic center of the head of the femur. Ankle joint center 16 is defined as the center of rotation of the ankle joint and is generally accepted to lie midway along an axis passing through the malleoli of the lower limb. Medial malleoli 20 exists on the distal end of the tibia. The lateral malloelus is a similar structure on the distal end of the fibula (not shown).

joint line 22 is a plane perpendicular to weight bearing axis 18 at a point approximating the bearing surface between femur 10 and tibia 12.

Figure 2B:
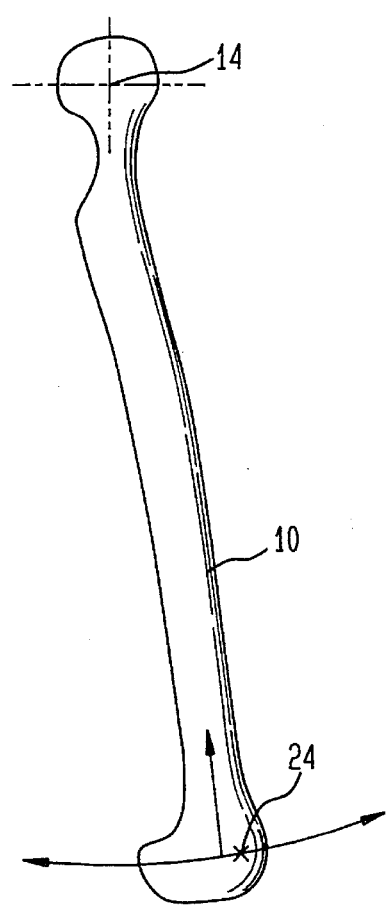

FIGS. 2a and 2b show in schematic form the motion of femur 10 about hip oint center 14 in the patient's coronal and sagital planes respectively.

The motion of femur 10 is governed by the ball socket hip joint such that, during any movement of femur 10, femoral registration point 24 fixed with respect to femur 10 will be constrained to move on the surface of a theoretical sphere with center at hip joint center 14 and radius equal to the distance between femoral registration point 24 end hip joint center 14.

By measuring the vectorial displacement between three successive positions of femoral registration point 24 in a reference frame in which hip joint center 14 remains stationary as femur 10 is moved, the position of hip joint center 14 in that reference frame can be calculated. Additionally, the location of hip joint center 14 with respect to femoral registration point 24 can also be calculated. Increasing the number of measured positions of femoral registration point 24 increases the accuracy of the calculated position of hip joint center 14.

Figure 3A:
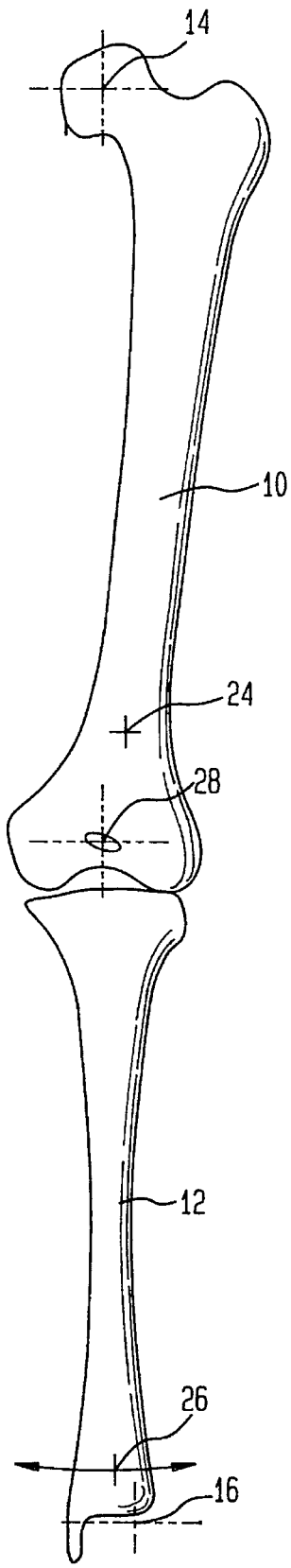
FIGS. 3a and 3b show simplified representations of the kinematic motion of the tibia with respect to the femur.
Figure 3B:
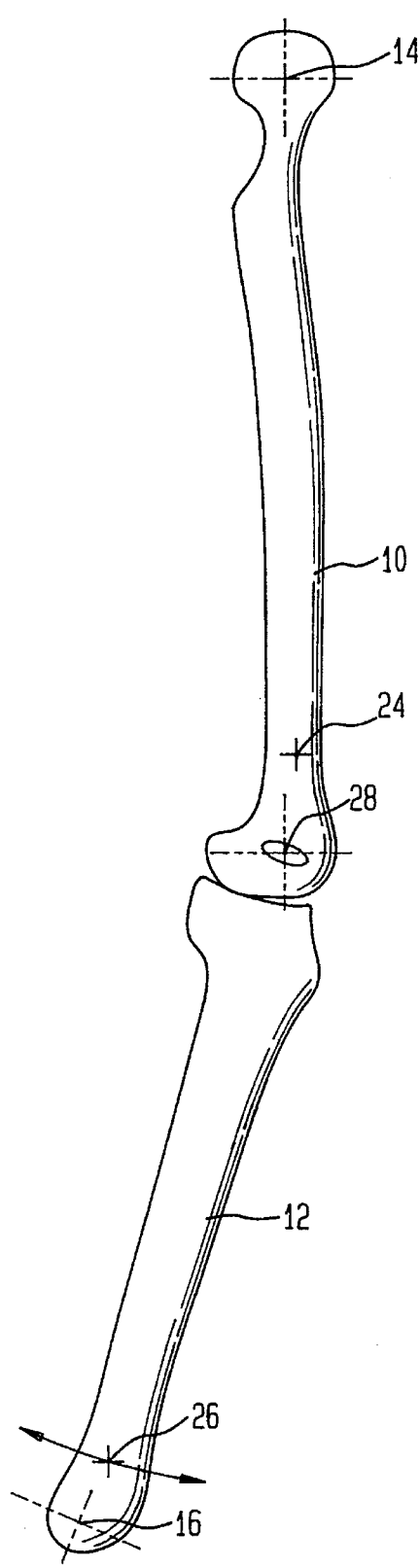

FIGS. 3a end 3b show in schematic form a simplified representation of the motion of tibia 12 with respect to femur 10 in the patient's coronal and sagital planes respectively.

The motion of tibia 12 with respect to femur 10 is a complex, six degree-of-freedom relationship governed by the ligamentous tension and the three bearing surfaces of the knee joint. However for the purposes of implant location, a reasonable approximation of the motion of tibia 12 can be made assuming the knee joint to be a sliding hinge in the sagital plane with limited motion in the coronal plane. Based on these simplifying assumptions, movement of tibial registration point 26 fixed with respect to tibia 12 will be constrained to move on the surface of a theoretical sphere with instantaneous center within the locus of knee joint center 28 and radius equal to the distance between tibial registration point 26 and knee joint center 28.

Because the bony nature of the human ankle permits intraoperative estimation of ankle joint center 16 by palpation, tibial registration point 26 can be fixed to tibia 12 at a known vectorial displacement from ankle joint center 16 through the use of a notched guide or boot strapped to the lower limb as is commonly known in knee arthroplasty. Measurement of the vectorial displacement of tibial registration point 26 with respect to femoral registration point 24, previously fixed-relative to femur 10 and at a calculated position relative to hip joint center 14, thereby permits the calculation of the vectorial position of ankle joint center 16 with respect to hip joint center 14 and the weight bearing axis to be determined. As with calculation of the position hip joint center 14, repeated measurements improve the accuracy of the determined weight bearing axis.

Further, by measuring the vectorial displacement between successive positions of tibial registration point 26 in a reference frame in which femoral registration point 24 remains stationary as tibia 12 is moved, the locus of positions of knee joint center 28 in that reference frame can be calculated.

Figure 4:
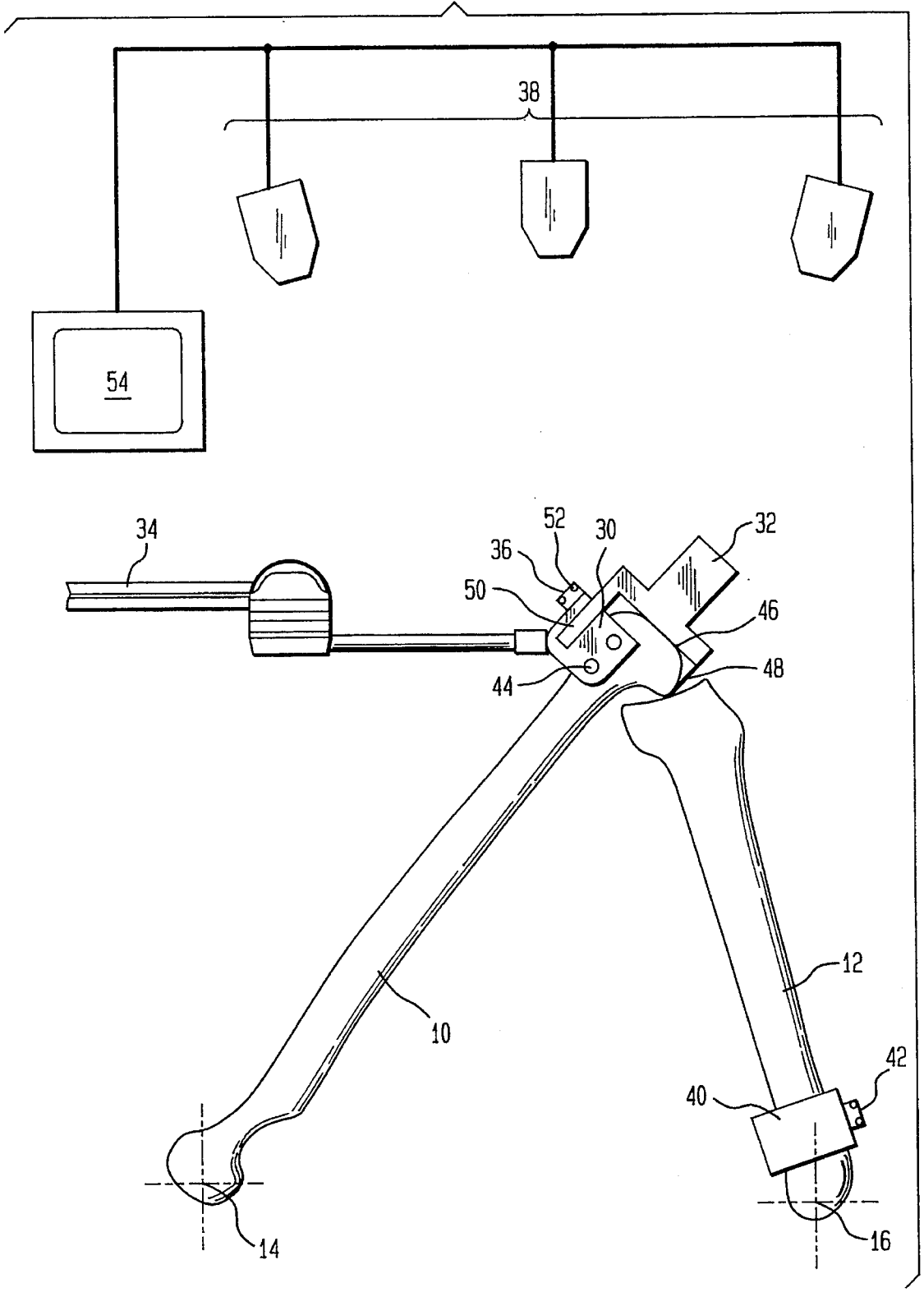
FIG. 4 shows apparatus for intraoperatively determining the weight bearing axis of the leg.

FIG. 4 shows apparatus useful for intraoperatively locating the joint centers and weight bearing axis of the human leg in a form useful for knee arthroplasty. Femur 10 and tibia 12 are shown in the patient's sagital plane, flexed to expose the surface of the knee joint for resurfacing. Although the leg has been shown in schematic, skeletal form for clarity, the apparatus is such that the soft tissues surrounding the leg and the protocols of the conventional operation are not negatively impacted by the use of the apparatus.

Registration clamp 30 can be attached to femur 10 so as to maintain a constant position with respect to femur 10. In the preferred embodiment fixation pins 44 placed in the medial and lateral surfaces of the distal femoral cortex assure rigid attachment of registration clamp 30 to femur 10 permitting the weight of the lower leg to be fully supported through registration clamp 30.

Alignment guide 32 permits registration clamp 30 to be attached to femur 10 at a determinant distance from the distal bearing surface of femur 10 and in known rotation about the anatomic axis of femur 10. Alignment guide 30 has a flat surface 46 which can be placed against the distal surface of femur 10 to set the displacement of registration clamp 30. Alignment guide 30 also has rotational alignment feature 48, which in the preferred embodiment is a thin shelf suitable for placement between femur 10 and tibia 12 while the knee is flexed and shaped to lie against the posterior medial and lateral bearing surfaces of femur 10. Alternatively, rotational alignment feature 48 may be shaped so as to use other common landmarks of the distal femur to set rotation. Alignment guide 50 also includes clamp location feature 50 which can be used to position registration clamp 30 prior to fixation to femur 10. Clamp location feature 50 may comprise slide rods or a tongue fitting into registration clamp 30 as are commonly used in knee arthroplasty instruments to locate cutting or alignment guides to the bones.

Support arm 34 is connected to registration clamp 30 and is used to rigidly position femur 10. In the preferred embodiment support arm 34 is a pneumatically lockable, flexible arm, such as is used in the Endex Endoscopy Positioning System (AndronicDevices Ltd., Richmond, B.C. Canada) which has sufficient strength to fully support the weight of the patient's lower limb above the table and has sufficient range of motion to permit the patient's leg to move through full flexion to full extension while attached to registration clamp 30. Support arm 34 is attached to the side of the operating table so as to remain stationary with respect to hip joint center 14.

Location marker 36 includes two or more light emitting features 52 visible to camera array 38. Camera array 38, object digitizing and display equipment 54 are used to measure the position and orientation of location marker 36 with respect to the reference frame in which camera array 38 is mounted. In the preferred embodiment camera array 38, object digitizing and display equipment 54, and location marker 36 comprise a system such as the "FlashPoint 3D Digitizer" (Pixsys, Boulder Colo.) which has the accuracy to resolve displacements of location marker 36 to within 0.1 mm within an operating volume similar to that of knee arthroplasty procedures. Location marker 36 is attachable to registration clamp 30 so as to remain fixed with respect to femur 10.

Ankle guide 40 is shaped to fit around the tissue of the patient's lower leg so as to remain fixed with respect to tibia 12 as it is moved. Ankle guide 40 preferably includes a V-notch feature, such as described by Petersen (U.S. Pat. No. 4,524,766) to intraoperatively locate ankle guide 40 at known displacement from ankle joint center 16. Ankle guide 40 further includes second location marker 42 identical in form and function to location marker 36 previously described. In the preferred embodiment both location marker 36 and second location marker 42 are employed although a single, repositioned marker could suffice.

Figure 5A:
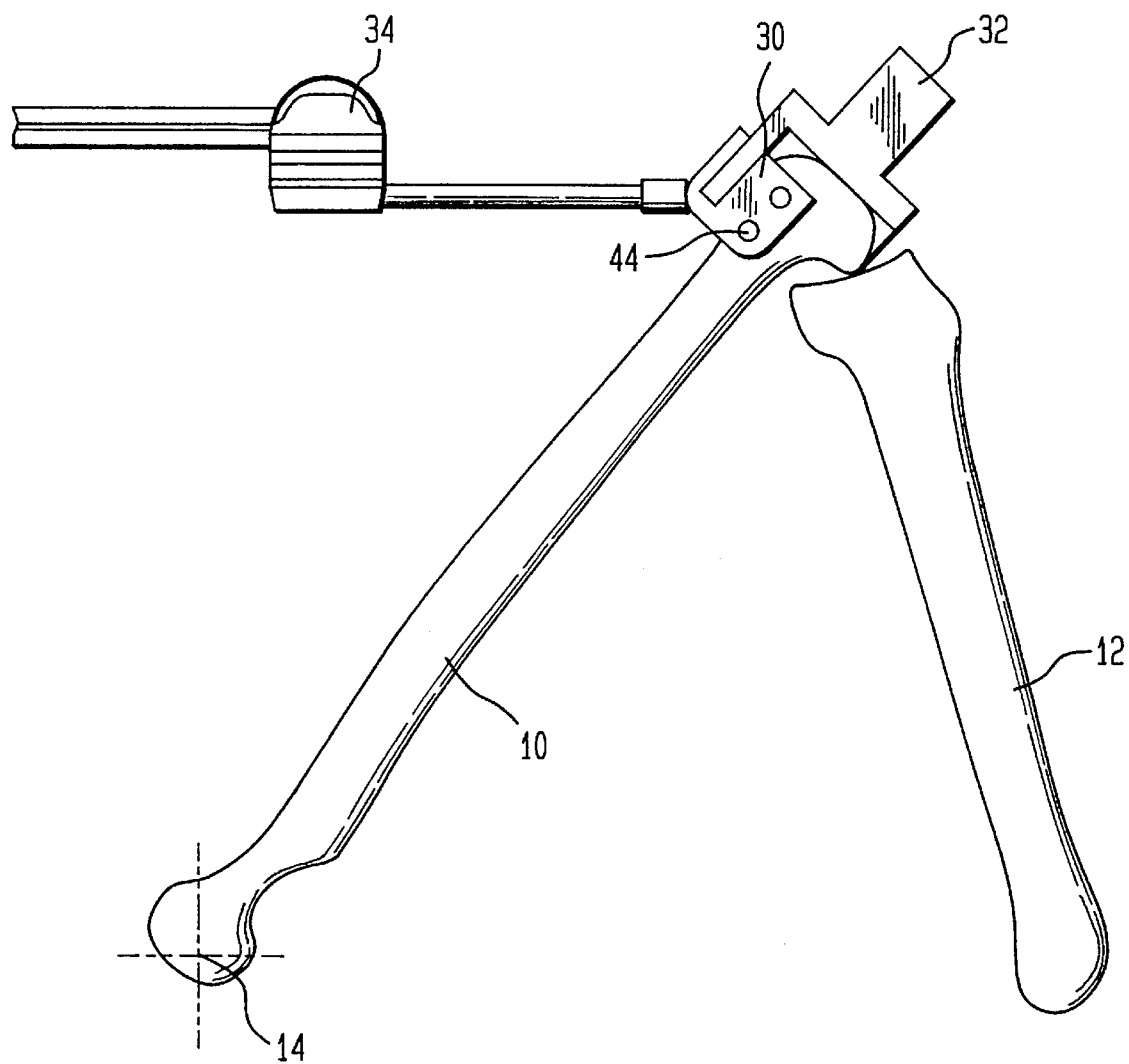
FIGS. 5a through 5c show a method for determining the weight bearing axis using he apparatus of FIG. 4.
Figure 5B:
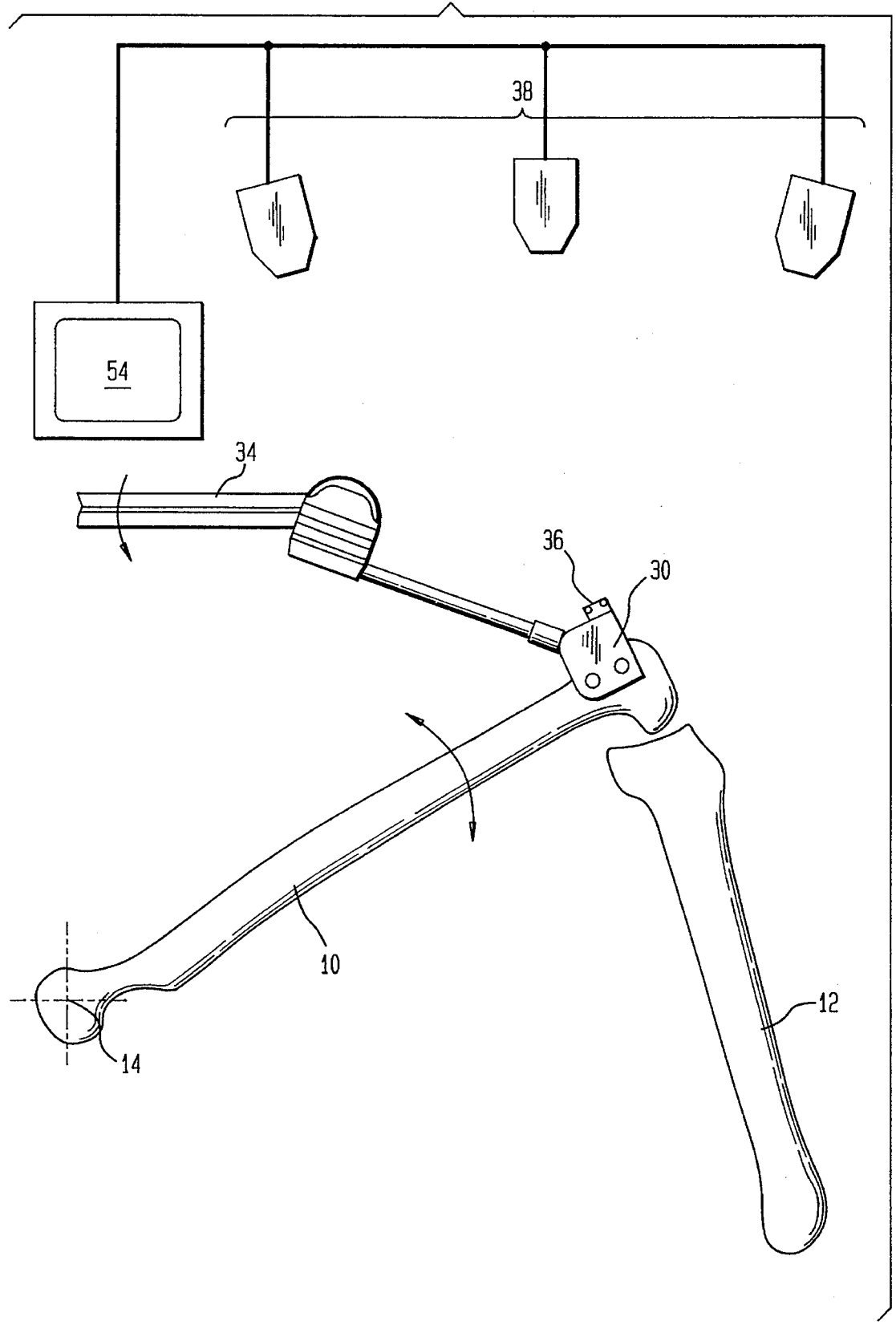
Figure 5C:
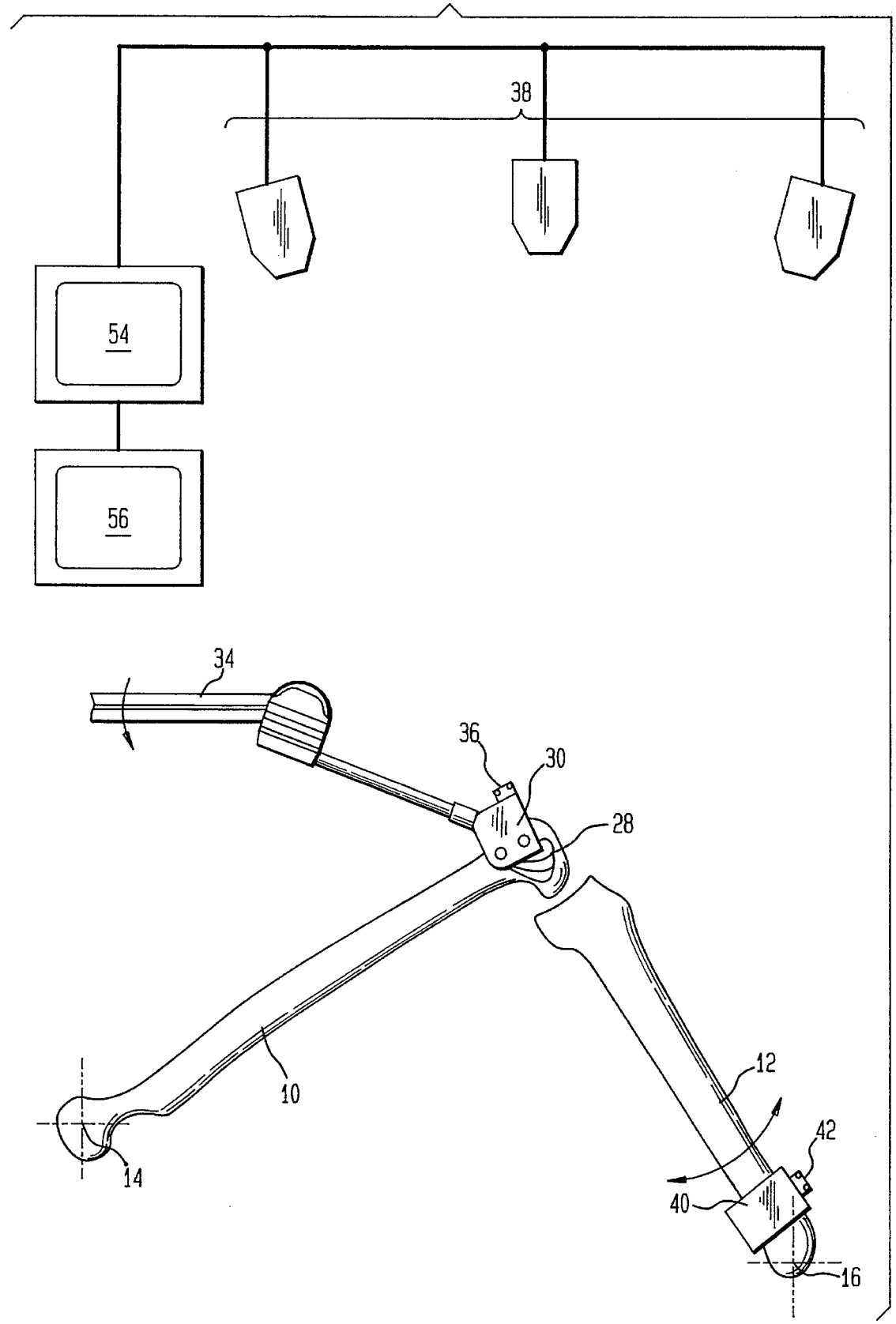

FIGS. 5a through 5c show the steps used to intraoperatively locate the patient's weight bearing axis using the apparatus of the current invention.

In FIG. 5a alignment guide 50 is placed over the distal end of femur 10 and used to set the position and rotation of registration clamp 30 with respect to femur 12. Fixation pins 44 are driven through registration clamp 30 for fixation to femur 10. Support arm 34, which is stationary with respect to hip joint center 14, may be connected to registration clamp 30 before or after it is affixed to femur 10. Tibia 12 is left to hang from femur 10 by the attaching ligaments.

In FIG. 5b, location marker 36 is attached to registration clamp 30. With support arm 34 unlocked, femur 10 is moved while the position of attached location marker 36 is measured and digitized by camera array 38 and object digitizing and display equipment 54. Following a minimum of three different measurements, object digitizing and display equipment 54 calculates the position of joint hip center 14 using the constraints that each measured point lies on the surface of a sphere centered at joint hip center 14 and that hip joint center 14 lies proximal to the attachment point of registration clamp 30. Repeated movements of femur 10 and locational measurements of location marker 36 are used to refine the accuracy of the calculated position of hip joint center 14 to within a desired range.

FIG. 5c shows how the apparatus of the current invention is used to locate ankle joint center 16 with respect registration clamp 30 thereby determining the weight bearing axis of the patient. While support arm 34 holds femur 10 fixed with respect to hip joint center 14 and camera array 38, ankle guide 40 and attached second location marker 42 re applied to tibia 12 at a known position relative to ankle joint center 16. At this point the position of second location marker 42 is measured and digitized by camera array 38 and object digitizing and display equipment 54 permitting ankle joint center 16 to be located with respect hip joint center 14 locating the patient's weight bearing axis with respect to registration clamp 30 and the distal landmarks on femur 10 used to position registration clamp 30. This information can then be displayed by object digitizing and display equipment 54 and used by the surgeon to guide resurfacing cuts on femur 10 and tibia 12.

Advantageously, support arm 34 provides sufficiently rigid positioning of femur 10 and registration clamp 30 with respect to hip oint center 14 that calculation of ankle joint center 16 with respect to hip joint center 14 is significantly simplified without the need to measure and locate registration clamp 30 at the same instant.

Further, tibia 12 can be repeatedly moved while the position of second location marker 42 is measured and digitized by camera array 38 and object digitizing and display equipment 54 permitting the locus of instantaneous knee centers 28 to be located with respect to ankle joint center 16, hip joint center 14 and registration clamp 30. This information can be used to refine the kinematic position of the knee oint with respect to registration clamp 30 beyond the initial bony landmark location provided by alignment guide 32.

information processing equipment 56 is included in the apparatus of this invention for receiving the digitized positions captured, calculated and displayed by object digitizing and display equipment 54, and for further processing this information into a suitable form that it may be used to direct robotic bone cutting equipment, such as described by Matsen at. el. (U.S. Pat. No. 4,979,949), in the performance of optimal bone cuts with respect to the patient's joint centers and weight bearing axis.

Many adaptations and alternations may be made to the embodiment described herein. Accordingly, the invention is to be limited only by reference to the appended claims. For example, although an optical system has been used to measure the position of reference points attached to the femur and tibia, these measurements could alternatively be performed with ultrasonic or magnetic emitters and receivers. Further direct measurement of the bone positions could be accomplished using precision resitive devices, such as linear variable displacement transducers (LVDTs) with one end attached to the bones and the opposite end placed in a known reference frame.

Additionally, gyroscopic equipment for precisely measuring angular changes, such as the GyroEngine (Gyration Inc., Saratoga, Calif.) could be applied to the bones to provide digitized signals representative of the angular positional changes measured in the bones. As the gyroscopes provide only angular measurement, further information is necessary to locate joint centers and this can be provided by moving the bones through a path of known distance while the angular changes are recorded, thus providing scaling information. Advantageously, the support am described can be used to limit the path of the bones to a known length while they are moved providing this scaling in a manner easily accomplished in the operating room.

We claim:

1. A method of intra-operatively locating the functional center of the hip for knee joint arthroplasty comprising the steps of:

(a) locating and marking a point on the femur of a patient;
   (b) holding the acetabulum of the patient relatively fixed so that displacement of the head of the femur is resisted;
   (c) repeating a minimum of three times the steps of:
       (i) rotating the femur to a discrete location; and, (ii) measuring a change in position of the marked point on the femur occurring to reach the discrete location; and (d) using the measured position changes to locate the center of an imaginary sphere, the surface of which includes all of the discrete locations, whereby said sphere center substantially corresponds to the center of the hip.

2. The method as claimed in claim 1, further comprising the step of supporting the femur with a support arm during the steps of rotating the femur and measuring the change in position.

3. The method as claimed in claim 1, wherein said step of locating and marking a point on the femur further comprises attaching a registration clamp to the femur at a determinant distance from the distal bearing surface of the femur and a known rotation about the anatomic axis of the femur.

4. The method as claimed in claim 1, wherein said step of locating and marking a point on the femur further comprises attaching a location marker with light emitting features.

5. The method as claimed in claim 1, wherein said step of measuring a change in position of the marked point on the femur further comprises locating a location marker using a camera array.

6. An apparatus for intra-operatively locating the functional center of the hip for knee joint arthroplasty comprising:

means for measuring changes in location of a point in space relative to a reference frame;

means for attaching the measurement means to a reference location on the femur of a patient;

means for holding the acetabulum of the patient fixed so that displacement of the head of the femur is resisted during rotation of the femur in the reference frame; and means for computing the location of an imaginary sphere from the measured changes in position of said reference location on the femur resulting from at least three discrete rotations of the femur about the femur head within the reference frame, said sphere location corresponding to the location of the functional center of the hip.

7. The apparatus as claimed in claim 6, wherein said means for measuring changes in location of a point in space relative to a reference frame further comprises a camera array.

8. The apparatus as claimed in claim 6, wherein said means for attaching the measurement means to a location on the femur further comprises a registration clamp for attaching to the femur at a determinant distance from the distal bearing surface of the femur and a known rotation about the anatomic axis of the femur.

9. The apparatus as claimed in claim 6, wherein said means for attaching the measurement means to a location on the femur further comprises a location marker with light emitting features.

10. A method of intra-operatively locating the weight bearing axis of the leg for knee joint arthroplasty comprising the steps of:

(a) locating the functional center of the hip by:
  (i) locating and marking a point on the femur of a patient;
  (ii) holding the acetabulum of the patient relatively fixed so that displacement of the head of the femur is resisted;
  (iii) repeating a minimum of three times the steps of:
    (1) rotating the femur to a discrete location; and,
    (2) measuring a change in of the marked point on the femur occurring to reach the discrete location;
  (iv) using the measured position changes to locate the center of an imaginary sphere, the surface of which includes all of the discrete locations, whereby said sphere center substantially corresponds to the center of the hip;

(b) locating a center of the ankle by:
  (i) locating and marking a point having a known relation to the ankle center;
  (ii) measuring a location of the marked point;

(c) using the location of the functional center of the hip and the center of the ankle to locate a line substantially corresponding to the weight beating axis.

11. An apparatus for intra-operatively locating the functional center of the hip for knee joint arthroplasty comprising:

a location marker having light emitting features, said location marker adapted for rigid attachment to the femur;

a camera array for measuring changes in location of said location marker relative to a reference frame;

a holding fixture for maintaining the acetabulum of the patient fixed so that displacement of the head of the femur in the reference frame is resisted; and digitizing and display equipment connected to said camera array for computing the functional center of the hip as a center of a theoretical sphere having on its surface three or more discrete positions of the location marker measured by the camera as the femur is rotated about the femur head relative to the reference frame.

* * * * *

UNITED STATES PATENT AND TRADEMARK OFFICE
CERTIFICATE OF CORRECTION

PATENT NO. : 5,611,353
DATED : March 18, 1997
INVENTOR(S) : Dance et al.

It is certified that error appears in the above-indentified patent and that said Letters Patent is hereby corrected as shown below:

Column 1, line 30, "8" should read --a--.

Column 1, line 49, "he" should read --the--.

Column 1, line 52, "o" should read --of--.

Column 1, line 52, after categories insert --:--

Column 2, line 9, "surgeon-skill" should read --surgeon skill--.

Column 2, line 19, "he" should read --the--.

Column 2, line 24, "o" should read --to--.

Column 2, line 25, "as result" should read --as a result--.

Column 2, line 29, "imply" should read --simply--

Column 2, line 54, "respect the" should read --respect to the--.

Column 2, line 56, "provide" should read --provided--.

UNITED STATES PATENT AND TRADEMARK OFFICE
CERTIFICATE OF CORRECTION

PATENT NO. : 5,611,353
DATED : March 18, 1997
INVENTOR(S) : Dance et al.

It is certified that error appears in the above-indentified patent and that said Letters Patent is hereby corrected as shown below:

Column 3, line 8, "he" should read --the--.

Column 3, line 31, "joint" should read --Joint--.

Column 3, line 35, "oint" should read --joint--

Column 3, line 37, "ball socket" should read --ball and socket--.

Column 3, line 42, "end" should read --and--

Column 4, line 12, "fixed-relative" should read --fixed relative--.

Column 4, line 44, "30" should read --32--.

Column 4, line 47, "30" should read --32--.

Column 4, line 54, "50" should read --32--.

Column 5, line 25, before "known" insert --a--.

UNITED STATES PATENT AND TRADEMARK OFFICE
CERTIFICATE OF CORRECTION

PATENT NO. : 5,611,353
DATED : March 18, 1997
INVENTOR(S) : Dance et al.

It is certified that error appears in the above-indentified patent and that said Letters Patent is hereby corrected as shown below:

Column 5, line 34, "50" should read --32--.

Column 5, line 36, "12" should read --10--

Column 5, line 62, "re" should read --are--.

Column 6, line 9, "oint" should read --joint--.

Column 6, line 20, "oint" should read --joint--.

Column 6, line 23, "information" should read --Information--.

Column 6, line 32, "alternations" should read --alterations--.

Column 8, line 31, "beating" should read --bearing--.

Signed and Sealed this

Twenty-seventh Day of May, 1997

BRUCE LEHMAN

Attest:

Attesting Officer

Commissioner of Patents and Trademarks